(12) United States Patent
Kim et al.

(10) Patent No.: US 12,067,903 B2
(45) Date of Patent: Aug. 20, 2024

(54) METHOD FOR MANUFACTURING FOOD INDICATOR

(71) Applicant: CJ CHEILJEDANG CORPORATION, Seoul (KR)

(72) Inventors: Grace Kim, Suwon-si (KR); Do Wan Kim, Suwon-si (KR); Kyoung Sik Cho, Suwon-si (KR); Seok Jun Hong, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 153 days.

(21) Appl. No.: 17/788,575

(22) PCT Filed: Dec. 24, 2020

(86) PCT No.: PCT/KR2020/019089
§ 371 (c)(1),
(2) Date: Jun. 23, 2022

(87) PCT Pub. No.: WO2021/133098
PCT Pub. Date: Jul. 1, 2021

(65) Prior Publication Data
US 2023/0043581 A1    Feb. 9, 2023

(30) Foreign Application Priority Data

Dec. 24, 2019  (KR) .................. 10-2019-0173831

(51) Int. Cl.
*G01N 33/12*      (2006.01)
*B32B 7/06*       (2019.01)
(Continued)

(52) U.S. Cl.
CPC .............. *G09F 3/0291* (2013.01); *B32B 7/06* (2013.01); *B32B 7/12* (2013.01); *B32B 27/36* (2013.01);
(Continued)

(58) Field of Classification Search
CPC ............ B32B 2255/10; B32B 2255/26; B32B 2307/7242; B32B 27/36; G09F 3/0291; G09F 2003/0257; C09D 11/033
See application file for complete search history.

(56) References Cited

U.S. PATENT DOCUMENTS 8,182,596 B2    5/2012  Kurihara et al.
8,425,996 B2 *  4/2013  Gorski ................. G01N 31/22
                                                    428/521
(Continued)

FOREIGN PATENT DOCUMENTS

CN    101273268 A    9/2008
CN    102405131 A    4/2012
(Continued)

OTHER PUBLICATIONS

PCT International Search Report for PCT Application No. PCT/KR2020/019089 mailed Apr. 8, 2021 (6 pages, with English translation).

(Continued)

*Primary Examiner* — Shin H Kim
(74) *Attorney, Agent, or Firm* — Merchant & Gould P.C.

(57) ABSTRACT

The present application relates to a method for manufacturing an indicator for food that can visually check the quality change in food in a package state, an indicator for food manufactured therefrom, and a method for checking the storage status of food using the same. The manufacturing method of an indicator for food of the present application includes bonding a first film, on which an indicator layer including a pH-sensitive indicator is formed on one surface thereof, and a second film, on which an adhesive layer is formed on one surface thereof, so that the indicator layer of the first film and the adhesive layer of the second film can face each other.

16 Claims, 5 Drawing Sheets

(51) Int. Cl.
  *B32B 7/12* (2006.01)
  *B32B 27/36* (2006.01)
  *B32B 37/12* (2006.01)
  *B65D 65/38* (2006.01)
  *C09J 7/25* (2018.01)
  *C09J 7/38* (2018.01)
  *G01N 21/78* (2006.01)
  *G01N 31/22* (2006.01)
  *G09F 3/00* (2006.01)
  *G09F 3/10* (2006.01)
  *G09F 3/02* (2006.01)

(52) U.S. Cl.
  CPC ............... *B32B 37/12* (2013.01); *C09J 7/255* (2018.01); *C09J 7/38* (2018.01); *G01N 31/221* (2013.01); *G09F 3/10* (2013.01); *B32B 2250/02* (2013.01); *B32B 2255/10* (2013.01); *B32B 2255/26* (2013.01); *B32B 2307/4023* (2013.01); *B32B 2307/4026* (2013.01); *B32B 2307/724* (2013.01); *B32B 2307/7242* (2013.01); *B32B 2439/70* (2013.01); *B32B 2519/00* (2013.01); *B32B 2553/00* (2013.01); *G09F 2003/021* (2013.01); *G09F 2003/0225* (2013.01); *G09F 2003/023* (2013.01); *G09F 2003/0257* (2013.01)

(56) References Cited

U.S. PATENT DOCUMENTS

| | | | |
|---|---|---|---|
| 2002/0011522 A1* | 1/2002 | Lawandy | G01N 31/229 428/521 |
| 2009/0301382 A1 | 12/2009 | Patel | |
| 2010/0196636 A1 | 8/2010 | Gorski et al. | |
| 2010/0215878 A1 | 8/2010 | Hurme et al. | |
| 2010/0275813 A1 | 11/2010 | Kurihara et al. | |
| 2013/0202531 A1* | 8/2013 | Gorski | B29C 66/45 424/9.1 |
| 2015/0268204 A1* | 9/2015 | Akiyama | G01N 21/783 426/87 |
| 2016/0349224 A1* | 12/2016 | Patel | G07C 1/00 |
| 2016/0356754 A1* | 12/2016 | Akiyama | G01N 33/12 |
| 2017/0131152 A1* | 5/2017 | Wötzer | B05D 1/02 |
| 2018/0016072 A1 | 1/2018 | Suryanarayanan et al. | |
| 2018/0110896 A1 | 4/2018 | Corzani et al. | |
| 2022/0243085 A1* | 8/2022 | Kim | B32B 7/12 |
| 2022/0412933 A1* | 12/2022 | Millman | G01N 31/229 |
| 2023/0043581 A1* | 2/2023 | Kim | B32B 7/12 |

FOREIGN PATENT DOCUMENTS

| | | |
|---|---|---|
| CN | 107179314 A | 9/2017 |
| CN | 104777162 B | 2/2018 |
| CN | 110415603 A | 11/2019 |
| JP | H07-49656 A | 2/1995 |
| JP | 2002-129139 A | 5/2002 |
| JP | 2008-195445 A | 8/2008 |
| JP | 2018-512298 A | 5/2018 |
| JP | 2018-517894 A | 7/2018 |
| KR | 2001-0046150 A | 6/2001 |
| KR | 2001-0110636 A | 12/2001 |
| KR | 2004-0070113 A | 8/2004 |
| KR | 2016-0043713 A | 4/2016 |
| KR | 10-1771224 B1 | 8/2017 |
| KR | 10-2018-0037736 A | 4/2018 |
| KR | 10-1860675 B1 | 5/2018 |
| KR | 10-1919772 B1 | 11/2018 |
| WO | 92-09870 A1 | 6/1992 |
| WO | 2009-060972 A1 | 5/2009 |
| WO | 2011-102216 A1 | 8/2011 |

OTHER PUBLICATIONS

PCT Written Opinion for PCT Application No. PCT/KR2020/019089 mailed Apr. 8, 2021.

Office Action issued on Jun. 26, 2023 for the corresponding Japanese patent application 2022-539244 (3 pages).

Office Action issued on Apr. 13, 2023 for the corresponding Chinese patent application 202080084737.X (9 pages).

Office Action issued on Sep. 8, 2023 for the corresponding Chinese patent application 202080084737.X (11 pages including English Translation).

Office Action issued on Dec. 11, 2023 for the corresponding Japanese patent application 2022-539244 (7 pages including English Translation).

Extended European Search Report issued on Dec. 19, 2023 for the corresponding European patent application 20904744.8 (8 pages).

* cited by examiner

[Fig. 1a]
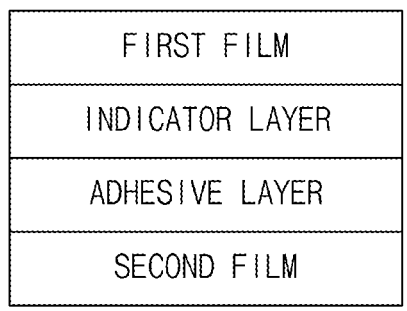
[Fig. 1b]
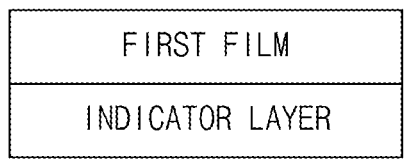
[Fig. 1c]
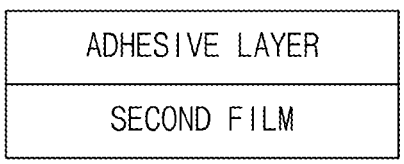

[Fig. 2]
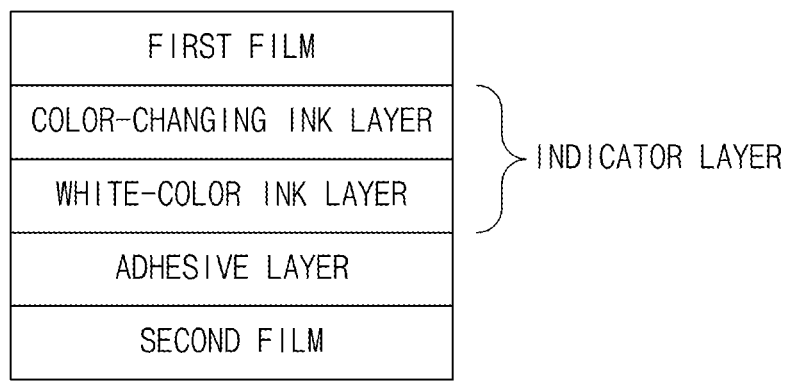
[Fig. 3]
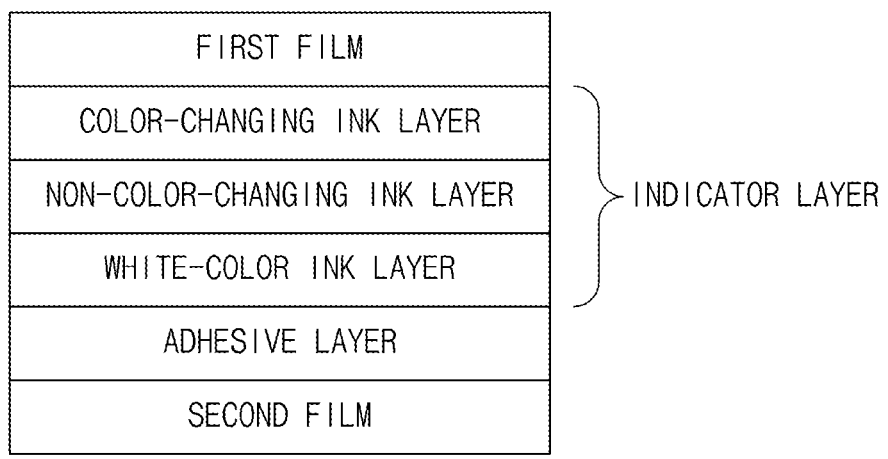

[Fig. 4]
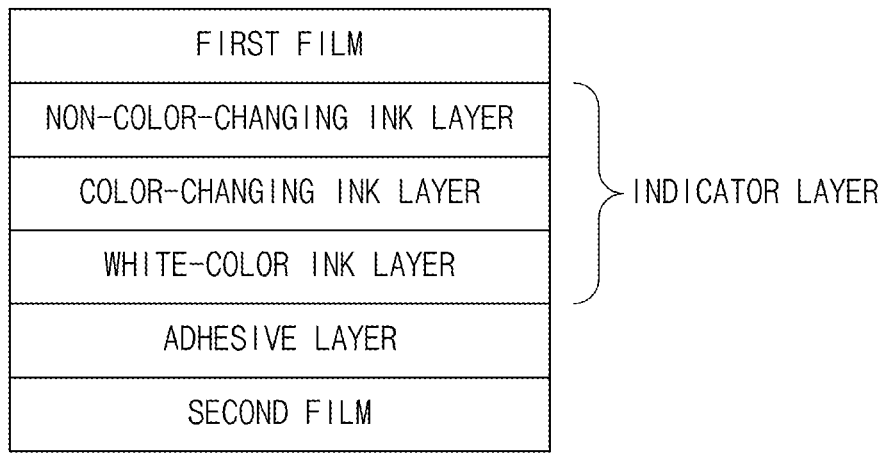
[Fig. 5]
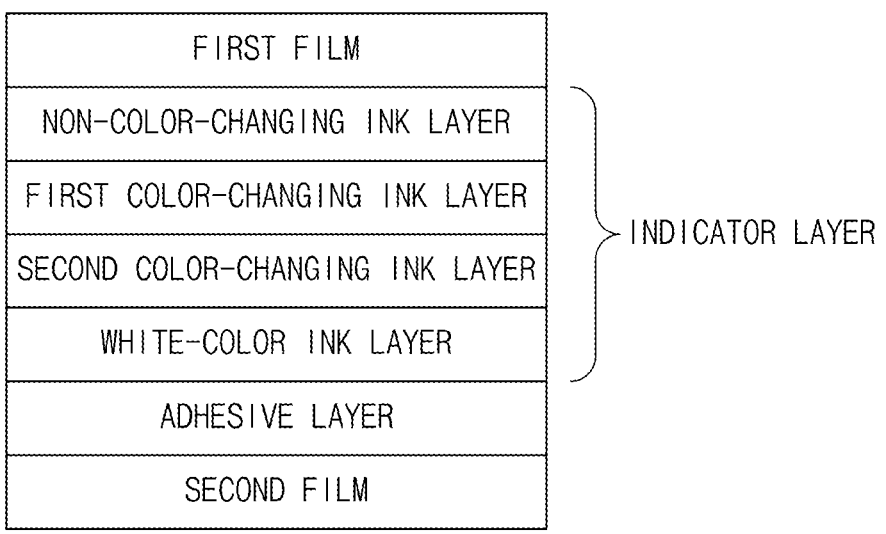

[Fig. 6]
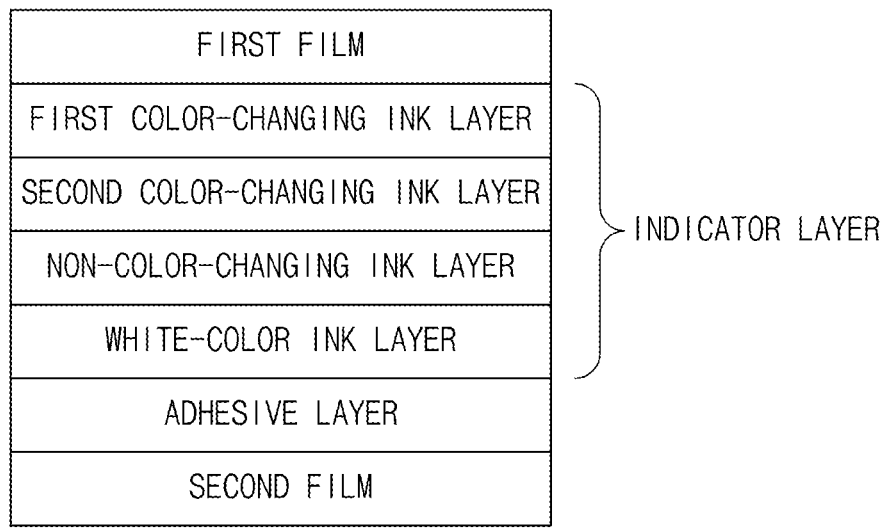
[Fig. 7]
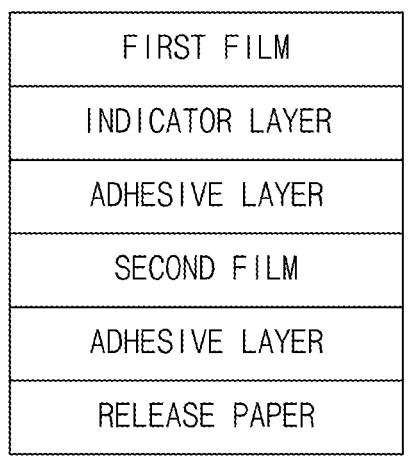

[Fig. 8]
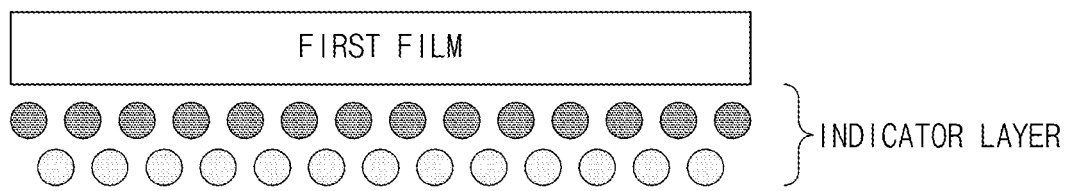
[Fig. 9]
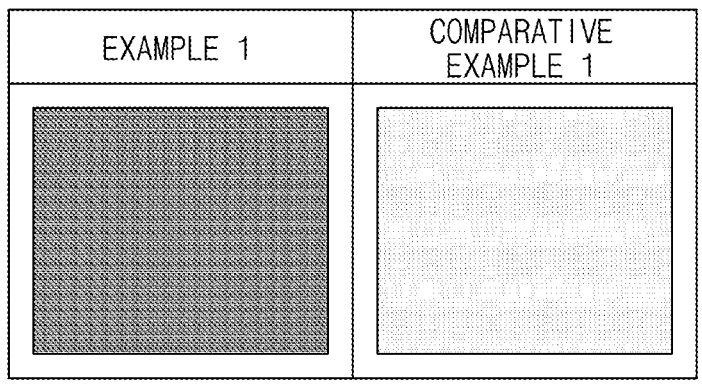
[Fig. 10]
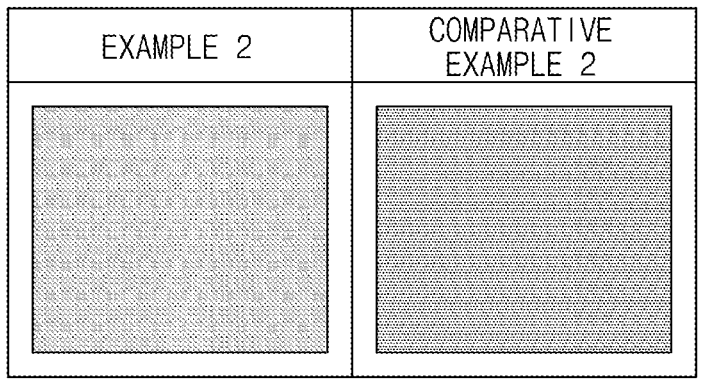

METHOD FOR MANUFACTURING FOOD INDICATOR

CROSS-REFERENCE TO RELATED APPLICATIONS

This application is a National Stage Application of PCT/KR2020/019089, filed 24 Dec. 2020, which claims priority to Ser. No. 10-2019-0173831, filed on 24 Dec. 2019, in the Republic of Korea and which applications are incorporated herein by reference. To the extent appropriate, a claim of priority is made to the above disclosed applications.

TECHNICAL FIELD

The present invention relates to an indicator for food that can visually check the quality change in food in a package state, and a manufacturing method thereof.

BACKGROUND ART

Color-changing inks that change colors using moisture, humidity, temperature, pH, UV exposure, pressure, gas contact, etc. as color-changing factors are being continuously studied and developed. In particular, in the field of food, indicators using a color-changing ink that can be visually confirmed by the naked eye by detecting changes in food during storage and distribution of food have been studied and developed so as to confirm food quality or food safety.

Since the indicators for confirming food quality or food safety should detect changes in food and display them in a form that can be visually confirmed, it is an important factor to secure the sensitivity to respond to small changes in the color-changing factor and the visibility for visual checking by the naked eye.

In order to secure the sensitivity and visibility of the indicators as described above, it is necessary to minimize the possibility of discoloration of these indicators from external color-changing factors, in addition to color-changing factors generated from food. For example, in the case of an indicator including a pH-sensitive color-changing ink that uses a pH change as a color-changing factor, external color-changing factors that change the pH present in the surrounding environment (e.g., carbon dioxide in the air, various volatile compounds, etc.) cannot be completely excluded in addition to color-changing factors generated from food; therefore, there is a demand for a technology that can minimize the possibility of discoloration from external color-changing factors.

In this regard, the present inventors have completed the present application in an effort to devise a method for minimizing the possibility of discoloration from external pH color-changing factors in the process of manufacturing an indicator for food including a pH-sensitive color-changing ink.

DISCLOSURE OF THE INVENTION

Technical Problem

An aspect of the present invention provides a method for manufacturing an indicator for food, which includes bonding a first film, on which an indicator layer including a pH-sensitive indicator is formed on one surface thereof, and a second film, on which an adhesive layer is formed on one surface thereof, so that the indicator layer of the first film and the adhesive layer of the second film face each other.

An aspect of the present invention provides an indicator for food formed with a first film, on which an indicator layer including a pH-sensitive indicator is formed, and a second film on which an adhesive layer is formed, in which is the indicator is manufactured by a method for manufacturing an indicator for food.

An aspect of the present invention provides a packaging material for food, which includes the indicator for food.

An aspect of the present invention provides the packaging material for food, and a food packaged by the packaging material for food.

An aspect of the present invention provides a method for checking the storage state of food using the indicator for food.

Technical Solution

According to an aspect of the present application, there is provided a method for manufacturing an indicator for food, which includes bonding a first film, on which an indicator layer including a pH-sensitive indicator is formed on one surface thereof, and a second film, on which an adhesive layer is formed on one surface thereof, so that the indicator layer of the first film and the adhesive layer of the second film face each other.

As used herein, the term "indicator layer" refers to a layer including a pH-sensitive indicator, and the pH-sensitive indicator can be formed by a composition including a pH-sensitive color-changing ink. The "pH-sensitive color-changing ink" may be one which uses a pigment that is discolored by a change in pH.

For example, the color-changing ink may be one which changes its color by an increase or decrease in pH; or one which changes its color by an increase or decrease in pH by a contact with a volatile gas (e.g., carbon dioxide, hydrogen sulfide ($H_2S$), acetic acid, etc.) and/or total volatile basic amine (e.g., trimethylamine (TMA), dimethylamine amine (DMA), oxygen ($O_2$), ammonia ($NH_3$)).

Meanwhile, the color-changing ink may be one which is discolored by a change in pH caused by a basic compound generated during decay of fish, chicken, beef, etc. Additionally, the color-changing ink may be one which, when the set carbon dioxide concentration used in the gas control packaging method is changed during storage of the food, is discolored by a change in pH caused by the altered concentration of carbon dioxide.

Additionally, the color-changing ink may be one which is discolored by a change in pH caused by carbamic acid formed when carbon dioxide reacts with a gas adsorbent material (e.g., PEI) in the indicator layer. Additionally, the color-changing ink may be one which is discolored by a change in pH caused by a reaction, in which carbonic acid is produced by the reaction between carbon dioxide and water ($H_2O$) formed by the reaction of materials generated during food storage.

Since the "indicator for food" including the indicator layer allows the user to visually check the pH change in the stored state of the food, for example, the storage state of the packaged food can easily be measured when the indicator for food is applied to a food packaging material. The effect of the indicator for food is not limited thereto, and the configuration of the indicator layer will be described later.

First, in order to manufacture an indicator for food, for example, a first film, on which an indicator layer including a pH-sensitive indicator is formed on one surface thereof, and a second film, on which an adhesive layer is formed on one surface thereof, are prepared; and the prepared first film and second film can be bonded so that the indicator layer of the first film and the adhesive layer of the second film can face each other.

In the present application, in illustrating the structure in which each layer of the indicator for food is formed, the "formation" means that the corresponding layer is interposed. The layer may be formed by a lamination method or may be formed by a printing method, and the method of formation is not particularly limited.

Referring to FIG. 1a, the indicator for food may include a structure in which a first film, an indicator layer, an adhesive layer, and a second film are sequentially formed. In addition, a plurality of layers having different functions may be included between each layer and the film, for example, a moisture transfer prevention layer, a heat conduction prevention layer, a gas penetration prevention layer, a light transmission prevention layer, etc. may additionally be interposed therebetween.

Referring to FIGS. 1b and 1c, an indicator layer including a pH-sensitive indicator may be formed on one surface of the first film according to the present application. An adhesive layer may be formed on one surface of the second film, and according to an embodiment, an adhesive composition may be applied or spray coated on one surface of the second film and dried to form the adhesive layer. The first film and the second film may be formed sequentially or simultaneously.

In one embodiment of the present application, the attachment of the first film and the second film may be performed after the adhesive composition is coated on one surface of the second film and dried. Specifically, after the adhesive layer is formed on one surface of the second film, the first film and the second film may be attached so that the adhesive layer faces the indicator layer of the first film. This is because when the adhesive composition forming the adhesive layer of the second film is attached to the indicator layer of the first film in an undried state, a color change of the indicator layer including a pH-sensitive indicator can be induced due to the volatilization of the pH adjusting agent, an acid component or volatile component in the adhesive composition, etc.

The adhesive composition forming the adhesive layer of the second film is not limited as long as it is an adhesive composition containing a component that can change the pH by volatilization, and specifically, the adhesive composition may be an aqueous solution-based adhesive, an emulsion-type adhesive, a solvent-type adhesive, a solvent-free adhesive, a solid-phase adhesive, a film-type adhesive, etc.

The aqueous solution-based adhesive may be, for example, a urea-based adhesive, a melamine-based adhesive, etc.; the emulsion-type adhesive may be a polyvinyl acetate-based adhesive, an acryl-based adhesive, etc.; the solvent-type adhesive may be an acryl-based, a chloroprene-based adhesive, a cellulose-based adhesive, a urethane-based adhesive, etc.; the solvent-free adhesive may be an epoxy-based adhesive, etc.; the solid-phase adhesive may be an ethylene vinyl acetate-based adhesive, an epoxy-based adhesive, etc.; and the film-type adhesive may bP a polyester-based adhesive, an epoxy-based adhesive, etc. More specifically, for uniform coating of the adhesive, an aqueous solution-based adhesive, an emulsion-type adhesive, a solvent-based adhesive, or a mixture thereof may be used.

More specifically, when an aqueous solution-based adhesive, an emulsion-type adhesive, a solvent-type adhesive, or a mixture composition thereof is used to form the adhesive layer, a pH change is caused by volatilization of a solvent (e.g., water, ethanol), a volatile binder, etc. in the adhesive composition during drying of the adhesive, the contact between the indicator layer and the adhesive layer may be performed after the adhesive composition applied to form the adhesive layer is dried. When the adhesive layer is sufficiently dried, a factor capable of inducing discoloration of the composition is transferred to the color-changing ink included in the indicator layer, and thereby it is possible to minimize discoloration that occurs.

In this case, whether the adhesive composition is sufficiently dried can be confirmed with the naked eye based on the presence/absence of color bleeding of the ink. More specifically, the sufficient drying may represent a state in which the volatile components including a solvent in the total adhesive composition of the adhesive layer are 1 wt % or less, more specifically 0.5 wt's or less, 0.3 wt % or less, 0.2 wt % or less, 0.1 wt % or less, or 0 wt % (i.e., no residue at all) or less, based on the weight of the adhesive composition before drying. The drying method of the adhesive composition may vary depending on the adhesive composition used to form the adhesive layer, for example, may be performed by methods such as room temperature drying, thermal drying, UV drying, etc., but is not limited thereto.

In one aspect, when the adhesive composition is thermally dried, the drying may be performed at a temperature, for example, at the vaporization temperature of the solvent in the adhesive or higher, but the temperature is not limited thereto. For example, in the case of an adhesive composition using an organic-based solvent such as ethanol, the drying of the adhesive may be performed at 60 to 100° C. after applying the adhesive.

As such, the effect of preventing discoloration of the indicator layer of the first film can be exhibited by contacting the second film and the first film so that the adhesive layer faces the indicator layer formed on the first film after the adhesive layer formed on the second film is dried.

Additionally, referring to FIG. 2, the indicator layer of the indicator for food according to another aspect may further include a white ink layer on one surface facing the adhesive layer. Additionally, the bonding of the first film and the second film may be the bonding of the first film and the second film so that the white ink layer and the adhesive layer are brought into contact.

Accordingly, the adhesive layer and the second film may be sequentially laminated on the white ink layer, and a structure in which another layer having a different function is interposed between each layer may be further included.

The white ink layer may serve to clearly indicate the color of the indicator layer, to thereby increase the visibility of the color change when the color of the indicator layer is changed. The white ink layer is formed of a composition containing white ink, and the white ink may use one or more kinds of pigments selected from the group consisting of inorganic pigments such as titanium dioxide, zinc oxide, lithopon, zinc sulfide (ZnS), lead white, and antimony shite, and white organic pigments.

The method of manufacturing the indicator for food in order to manufacture the indicator for food including the white ink layer as described above may include a step of forming a white ink layer using white ink on one side of the indicator layer, before contacting one side of the indicator layer formed on one side of the first film with the adhesive layer of the second film. In particular, the surface which is brought into contact with the adhesive layer is a white ink layer interposed on the outermost side of one surface of the indicator layer.

In another aspect, when the white ink layer is formed on the outermost side of the indicator layer, there may be a problem in that the indicator layer is discolored by the pH of the white ink itself or by gas volatilization while drying the white ink composition. Accordingly, the effects of increasing the visibility of the color change of the indicator layer and improving the accuracy of food quality confirmation may also be exhibited by forming the second film as a white film without forming a white ink layer on the outermost side of the indicator layer.

In the indicator for food, the indicator layer formed on one surface of the first film may be formed to include a pH-sensitive color-changing ink and a non-color-changing ink. For example, the indicator layer may be formed in such a form where a pH-sensitive color-changing ink and a non-color-changing ink are mixed in a single layer.

Additionally, the indicator layer formed on one surface of the first film may be formed by alternately printing at least one pH-sensitive color-changing ink and at least one non-color-changing ink on one surface of the first film. Specifically, the alternation may mean printing the color-changing ink and the non-color-changing ink in an alternate fashion. Additionally, the alternation may mean that the color-changing ink and the non-color-changing ink form a different single layer to thereby exhibit a repeated structure.

More specifically, the indicator layer formed on one surface of the first film may be formed by alternately printing in a gravure method by alternating at least one pH-sensitive color-changing ink and at least one non-color-changing ink on one surface of the first film. Additionally, the printing method of the indicator layer formed on one surface of the first film may be performed by various printing methods such as flexographic printing, silk screen printing, digital printing, etc., but is not limited thereto, and may be performed by a printing method other than the above-described method as necessary.

Specifically, the indicator layer may be formed from a composition containing a pH-sensitive color-changing ink and a non-color-changing ink, and may be formed from each of a composition containing a pH-sensitive color-changing ink and a composition containing a non-color-changing ink. For example, referring to FIGS. 3 to 6, the indicator for food may include at least one pH-sensitive color-changing ink layer and at least one non-color-changing ink layer. In the present application, when the indicator for food includes two or more of a color-changing ink layer and a non-color changing ink layer, respectively, these layers may be named the first color-changing ink layer, the second color-changing ink layer, the first non-color-changing ink layer, and the second non-color changing ink layer in the order of being closest to the first film.

FIG. 8 is a schematic diagram according to an embodiment in which two ink layers constitute an indicator layer on the first film. In particular, the ink layer close to the first film may be a color-changing ink layer and the next layer may be a non-color-changing ink layer; or an ink layer close to the first film may be a non-color-changing ink layer, and the next layer may be a color-changing ink layer, and the technical idea is not limited thereto.

Referring to FIG. 8, the method may include printing at least one of the compositions including the color-changing ink and the composition including the non-color-changing ink by a gravure method. For example, two ink layers may be printed on the first film by a gravure method, and a color-changing factor may be transferred to a space between the printed inks to induce discoloration of the color-changing ink. Additionally, in particular, the visibility can be improved through realization of a mixed color by mixing the colors of the two printed ink layers. Specifically, the indicator layer formed of only the color-changing ink has a problem in that the color change may not appear clearly due to the low brightness of the color. When the color-changing ink and the non-color-changing ink are mixed and printed, or the colors of each layer are seen mixed, the color change can be displayed more clearly.

The indicator layer may be a single layer formed from a single composition including a color-changing ink and a non-color-changing ink, and may include a color-changing ink layer formed from a color-changing ink composition and a non-color-changing ink layer formed from a non-color-changing ink composition, respectively. In contrast, in the case where the indicator layer is composed of a color-changing ink alone, if the indicator layer, which is formed into a color-changing ink layer and a non-color-changing ink layer from each of a color-changing ink and a non-color-changing ink, is manufactured, compared to the indicator layer which is formed as a single layer with the same thickness by mixing a color-changing ink and a non-color-changing ink, the total amount of the color-changing pigment used may be increased. In this case, it may cause a problem that the cost of the indicator for food increases. Additionally, when the indicator layer is formed from a mixed composition by mixing a color-changing ink and a non-color-changing ink, there may be a problem in that the compatibility of the color-changing ink and the non-color-changing ink should be considered because the color-changing ink and the non-color-changing ink should be evenly mixed. Accordingly, the indicator layer may be formed by mixing a color-changing ink and a non-color-changing ink so as to improve economic efficiency and process simplification when manufacturing the indicator for food.

In this way, the visibility of the indicator layer can be improved by mixing a color-changing ink and a non-color-changing ink. Additionally, in forming the indicator layer, the amount of the color-changing ink used in the process of forming the indicator layer may be reduced by way of using a non-color-changing ink, and thereby the effect of cost reduction can be expected.

For the color-changing ink, a pigment whose color is changed by a pH change may be used. The type of pigments to be used may include, for example, one or more kinds of pigments selected from the group consisting of Alizarin Blue, Methyl Violet, o-Cresol Red, Crystal Violet, Erythrosin, Thymol Blue, m-Cresol Red, Methyl Violet 6B, Aminoazobenzene, Alizarin Yellow R, β-dinitrophenol (2,6-dinitrophenol), Methyl Orange, Congo Red, p-Ethyl Orange, Naphthyl Red, Methyl Red, carminic acid, Chlorophenol Red, Bromothymol Blue, Phenol Red, Neutral Red, and phenolphthalein, but the pigments are not particularly limited thereto.

As for the non-color-changing ink, any ink can be used as long as the ink does not change its color by the color-changing factor to be confirmed using an indicator for food, and specifically, any ink that does not change its color by the color-changing factor of the color-changing ink can be used. More specifically, the non-color-changing ink may use a pigment that does not change its color by a change in pH.

The type of the non-color-changing ink is not particularly limited. For example, as the non-color-changing ink, those which do not change their colors by external environmental factors, while making the color change in the mixed color more distinct when they are mixed with a color-changing ink thereby improving visibility. For example, for the non-color-changing ink, at least one pigment implementing white, yellow, red, brown, green, blue, black, gold, and silver colors or a mixed color thereof may be used alone or in combination.

The pigment content in the ink composition for forming the indicator layer (e.g., a color-changing ink composition, a non-color-changing ink composition, or a mixed composition of color-changing ink and non-color-changing ink) may be such that, for example, the color-changing ink is included in an amount of 1 wt % to 10 wt %, and the non-color-changing ink is included in an amount of 0.05 wt % to 2 wt % based on the total weight of the ink composition, but is not limited thereto.

For example, when the composition of the pigment in the ink composition is included in the above range and the color-changing ink and the non-color-changing ink are mixed to form the indicator layer, the visibility of the indicator layer may be increased compared to when the non-color-changing ink is not used, despite the decrease in the degree of change in the indicator layer by reducing the content of the color-changing ink. More specifically, in the indicator layer in which the color-changing ink and the non-color-changing ink are mixed, the conditions such as the color, brightness, and chroma of the initial indicator layer can easily be contrasted with the conditions of the final indicator layer, such as the color, brightness, and chroma of the indicator layer, thus enabling easy identification of changes in the indication layer.

The indicator layer may further include an adsorbent material for the color-changing factor so as to improve the adsorption property of the color-changing factor, in addition to the pH-sensitive color-changing ink and the non-color changing ink. The adsorbent material may adsorb gas generated from food. Then, by-products or hydrogen ions may be generated through a reaction between the adsorbent material and the gas and thereby induce the discoloration of the pH-sensitive color-changing ink. These adsorbent materials may selectively react with a specific gas, thereby improving the reactivity.

For example, the adsorbent may include a gas adsorbent material, and specifically may include a hydroxide. The hydroxide may be, for example, calcium hydroxide, lithium hydroxide, potassium hydroxide, sodium hydroxide, or a mixture thereof, but is not limited thereto. The adsorbent material may be included, for example, in an amount of 1 wt to 10 wt % based on the total weight of the ink composition for forming the indicator layer, but is not limited thereto. Additionally, when the indicator layer is composed of at least one color-changing ink layer and at least one non-color-changing ink layer, the adsorbent material may be included in the at least one color-changing ink layer.

The indicator layer may be formed by direct application or spray onto the first film. Since the first film is disposed on the external environment side rather than the packaged food within the indicator for food, the first film may be a non-breathable film so as not to induce discoloration of the indicator layer.

In order to implement the first film to be non-breathable, the first film may be formed of a non-breathable material, or the first film may be formed to be thick so as to prevent the penetration of the color-changing factor or to allow a low amount of gas permeation amount. For example, the first film may be formed of one or more materials selected from the group consisting of polyethylene terephthalate (PET), nylon (polyamide), and polyvinyl chloride (PVC). Additionally, the first film may be formed to have a thickness of 12 μm to 30 μm.

The second film may be composed of a breathable film so that the change in pH resulting from a change in the quality of packaged food and/or the occurrence of gas generation that can cause a change in pH can be transferred to the indicator layer on the first film using an indicator for food.

The second film may be formed of a breathable material so as to exhibit air permeability, or may be formed as a thin layer to exhibit air permeability. Additionally, the second film may be formed of a hydrophilic material to exhibit a property of transferring internal pH change and/or moisture particles generated by gas generation that can cause pH change to the indicator layer, but the mechanisms that allow the second film to have air permeability are not limited thereto.

When the second film is formed of a breathable material, such a breathable material may be one or more materials selected from the group consisting of linear low-density polyethylene (LLDPE), low-density polyethylene (LDPE), high-density polyethylene (HDPE), polypropylene (PP), Tyvek®, paper, cellulose triacetate, and Pebax® elastomer.

In one aspect, the second film may be formed of a barrier material, in addition to the above-described breathable material, in the case of a food in a food packaging material that takes a long period of time to decompose. The barrier material may be formed of, for example, one or more materials selected from the group consisting of polyethylene terephthalate (PET), nylon (polyamide), and polyvinyl chloride (PVC). Additionally, the barrier material may be a second film formed at this time processed to show air perforation by forming a perforation, and in particular, the perforation may have a diameter of 0.5 to 50 μm. Additionally, the second film may be formed to a thickness of 50 to 100 μm so as to exhibit air permeability.

As described above, the second film is formed of a white film, and thus, it can exhibit the effect of clearly displaying the color of the indicator layer without the white ink layer in the indicator for food.

The indicator for food may be directly printed on a food packaging material, or manufactured in the form of a label and attached to a food packaging material.

In one aspect, the method for manufacturing the indicator for food may include attaching a release paper to the rear surface of the second film. Accordingly, as shown in FIG. 7, the indicator for food may be manufactured in the form of a label to be attached to a food packaging material, such that it forms an adhesive layer on the rear surface of the second film and includes a release paper.

In one aspect, the present application can provide a packaging material for food including the indicator for food.

The food packaging material is not particularly limited as long as it is used for packaging food. For example, as the packaging material for food including the indicator for food, a material such as paper, glass, can, metal such as metal foil, cellophane, plastic, etc., and a multi-layer material using the same may be used. In one embodiment, the plastic may be polyethylene (PE), polypropylene (PP), polystyrene (PS), polyvinyl chloride (PVC), polyester (PET), polyimide (PA or nylon), polyvinyl alcohol (PVA), polycarbonate (PC), polyvinylidene chloride (PVDC), cellulose, phenol resin, urea resin, melamine resin, epoxy resin, etc.

In one aspect, the present application can provide a packaged food which includes the food packaging material and the food included in the food packaging material.

The type of food included in the food packaging material is not particularly limited, but it may be a food group requiring measurement of freshness or a food group requiring confirmation of food deterioration. Such food types may include, for example, fresh meat (beef, pork, chicken, duck, fish, etc.), processed meat (ham, fish cake, bacon, sausage, salted meat, beef jerky, hot dog, Char siu, grilled fish, etc.), fermented food (kimchi, jeotgal (salted seafood), paste, etc.), etc.

In one aspect, the present application can provide a method for confirming the quality of food using the indicator for food manufactured as described above, for example, a method for checking the storage state of the food.

In one embodiment, the method of confirming the storage state of the food may include visually detecting a color change of the indicator layer. Additionally, the method may be confirming whether there is a change in food quality from the color change of the indicator layer.

For example, the indicator for food may express the freshness of the food in green and the change in food quality in yellow. In this case, through the method of confirming the storage state of the food, it can be confirmed that the green state is a state in which the food is stored stably and there is no change in quality, and the yellow state can predict spoilage, denaturation, etc. of the food.

More specifically, the indicator for food displays green in the pH range in which the initial food is packaged, whereas when the pH is changed by the gas generated from the food and deviates from the preset standard, the color may be changed to yellow. In this case, the consumer can recognize the change in the quality of the food through the discoloration state of the indicator for food, and can confirm the storage state of the food through the same. Meanwhile, the color indicated by the indicator for food is not limited to the above exemplary embodiment, and may be changed and applied according to the characteristics of the color-changing ink or non-color-changing ink included in the indicator layer.

As such, the consumers can confirm the storage state of the stored food based on the color according to the color-changing ink and the non-color-changing ink included in the indicator layer of the indicator for food.

Advantageous Effects

When the manufacturing method of an indicator for food is used, it is possible to provide an indicator for food including an indicator capable of confirming a change in the quality of packaged food, for example, a change in pH.

Additionally, when the manufacturing method of an indicator for food is used, it is possible to provide an indicator for food with significant improvement on the accuracy of confirming food quality and a packaging material for food including the same, by allowing the color-changing ink included in the indicator for food to maintain the color before discoloration prior to the use of the indicator for food.

BRIEF DESCRIPTION OF THE DRAWINGS

FIG. 1a is a chart schematically illustrating the structure of an indicator for food according to an embodiment. Specifically, the indicator for food may be formed by laminating two structures previously prepared as shown in FIGS. 1b and 1c.

FIG. 2 is a chart schematically illustrating the structure of an indicator for food according to an embodiment.

FIG. 3 is a chart schematically illustrating the structure of an indicator for food according to an embodiment.

FIG. 4 is a chart schematically illustrating the structure of an indicator for food according to an embodiment.

FIG. 5 is a chart schematically illustrating the structure of an indicator for food according to an embodiment.

FIG. 6 is a chart schematically illustrating the structure of an indicator for food according to an embodiment.

FIG. 7 is a chart schematically illustrating the structure of an indicator for food according to an embodiment.

FIG. 8 is a schematic drawing illustrating a method of printing an indicator layer on a first film according to an embodiment.

FIG. 9 is an image showing the colors of the indicators for food of Example 1 (left) and Comparative Example 1 (right).

FIG. 10 is an image showing the colors of the indicators for food of Example 2 (left) and Comparative Example 2 (right).

MODE FOR CARRYING OUT THE INVENTION

Hereinafter, the present application will be described in more detail.

EXAMPLE 1

Preparation of Indicator for Food

After forming an indicator layer on a first film and forming an adhesive layer on a second film, upon completion of drying of an adhesive layer, a pre-formed indicator layer was attached to prepare an indicator for food.

Specifically, a color-changing ink composition was prepared using ethanol as a solvent by stirring 100 parts by weight of a urethane-based binder, 2 parts by weight of a color-changing ink, and 5 to 7 parts by weight of a gas adsorbent material.

The color-changing ink composition was composed of a mixture of Methyl Red, Bromothymol Blue, Thymol Blue, and Phenolphthalein.

Thereafter, a yellow non-color-changing ink composition was printed on a 12 μm PET film (the first film) by a 175 line gravure method, and then dried. The color-changing ink composition prepared above was printed by the 175 line gravure method on a PET film, on which non-color-changing ink had been printed, and then dried. A white ink composition was printed on the color-changing ink layer formed above and then dried (formation of an indicator layer).

Then, the second film was coated with a urethane-based adhesive and dried at 70° C. for a few seconds. After drying, the residual solid content was made to be 20 wt % to 30% of the applied adhesive composition (formation of an adhesive layer).

After laminating the indicator layer and the adhesive layer formed above by lamination, an adhesive was applied to the outer surface of the second film, and then a release paper was attached thereto and aged under a 40° C. to 50° C. condition to prepare an indicator for food.

COMPARATIVE EXAMPLE 1

Preparation of Indicator for Food

An indicator for food was prepared by sequentially forming an indicator layer, an adhesive layer, and a second film on the first film using the components used in Example 1.

As a result of the experiment, the images of Example 1 and Comparative Example 1 prepared above are shown in FIG. 9, and the color values of Example 1 and Comparative Example 1 are shown in Table 1 below.

TABLE 1

| | Example 1 | | | Comparative Example 1 | | |
|---|---|---|---|---|---|---|
| HSV Color Data | Hue 126° | Saturation 61.0% | Value 48.2% | Hue 112° | Saturation 55.6% | Value 60.0% |
| RGB Hex Code | | 307B38 | | | 4F9944 | |

As can be seen in FIG. 9 and Table 1, the indicator for food of Example 1, in which the adhesive was printed on the second film, dried, and laminated with the indicator layer, showed a color difference after discoloration compared to the color before discoloration, according to the pH discoloration section. In particular, it was confirmed that since the used color-changing ink changes to yellow (H60) when discolored, the visibility of the indicator for food of Comparative Example 1 with an H value of 120° or less was decreased, whereas the indicator for food of Example 1, in which discoloration was minimized by external color-changing factors, could improve the visibility by increasing the color change greater when confirming the quality.

EXAMPLE 2

Preparation of Indicator for Food

An indicator for food was prepared in the same manner as in Example 1, except that an indicator layer was prepared by mixing 100 parts by weight of an ethanol-based urethane binder, 2 parts by weight of a mixture of Methyl Red, Bromothymol Blue, Thymol Blue, and Phenolphthalein as a color-changing ink, 2 parts by weight of a red pigment as a non-color-changing ink, and 2.5 parts by weight of PEI as a gas adsorbent material.

COMPARATIVE EXAMPLE 2

Preparation of Indicator for Food

An indicator for food was prepared in the same manner as in Example 1, except that an indicator layer was prepared by mixing 100 parts by weight of an ethanol-based urethane binder, 2 parts by weight of a mixture of Methyl Red, Bromothymol Blue, Thymol Blue, and Phenolphthalein as a color-changing ink, and 2.5 parts by weight of PEI as a gas adsorbent material.

The images of Example 2 and Comparative Example 2 prepared above are shown in FIG. 10 and the color values are shown in Table 2 below.

TABLE 2

| | Example 2 | | | Comparative Example 2 | | |
|---|---|---|---|---|---|---|
| HSV Color Data | Hue 356° | Saturation 25.3% | Value 69.8% | Hue 106° | Saturation 14.0% | Value 70.2% |
| RGB Hex Code | | B28588 | | | A0B39A | |

As can be seen in FIG. 10 and Table 2, it was confirmed that the indicator for food of Example 2, in which a color-changing ink and a non-color-changing ink were used together, shows the initial color before discoloration so that the color change can be greater compared to the indicator for food of Comparative Example 2.

As a result of the experiment, as shown in FIG. 10 and Table 2, for the indicator for food of Example 2 includes a scarlet pigment, the initial color was set to purple, and the final color was set to orange. In contrast, for the indicator for food of Comparative Example 2 prepared without a scarlet pigment, and the initial color was set to blue, and the final color was set to yellow under the same conditions. As such, it was confirmed that the brightness, saturation, and color of the indicator layer were improved by the scarlet pigment, which is a kind of non-color-changing ink included in Example 2, and visibility was improved through the same.

The invention claimed is:

1. A method for manufacturing an indicator for food, the method comprising:
bonding a first film, on which an indicator layer comprising a pH-sensitive indicator is formed on one surface thereof,
and a second film, on which an adhesive layer is formed on one surface thereof, so that the indicator layer of the first film and the adhesive layer of the second film face each other,
wherein the indicator layer further comprises a white ink layer on one surface facing the adhesive layer, and
in the bonding of the first film and the second film, the first film and the second film are bonded so that the white ink layer and the adhesive layer are brought into contact.

2. The method for manufacturing an indicator for food of claim 1,
wherein the adhesive layer of the second film is formed by coating an adhesive composition on one surface of the second film,
in which the adhesive composition comprises a volatile component, and the volatile component is comprised to be 1 wt % or less based on the total weight of the adhesive composition.

3. The method for manufacturing an indicator for food of claim 1, wherein the adhesive layer of the second film is formed by coating an adhesive composition on one surface of the second film followed by drying, and
the bonding of the first film and the second film is performed after the adhesive composition coated on one surface of the second film is dried.

4. The method for manufacturing an indicator for food of claim 1, wherein the adhesive layer of the second film is formed by coating an aqueous solution-based adhesive, an emulsion-type adhesive, a solvent-type adhesive, or a mixture thereof on one surface of the second film.

5. The method for manufacturing an indicator for food of claim 1, wherein the indicator layer of the first film is formed by comprising a pH-sensitive color-changing ink and a non-color-changing ink.

6. The method for manufacturing an indicator for food of claim 1, wherein the indicator layer of the first film is formed by alternately printing at least one pH-sensitive color-changing ink and at least one non-color-changing ink on one surface of the first film.

7. The method for manufacturing an indicator for food of claim 1, wherein the indicator layer of the first film is formed by printing by a gravure method by alternating at least one pH-sensitive color-changing ink and at least one non-color-changing ink on one surface of the first film.

8. The method for manufacturing an indicator for food of claim 1, wherein the indicator layer comprises a gas adsorbent material.

9. The method for manufacturing an indicator for food of claim 1, wherein the second film is a white film.

10. The method for manufacturing an indicator for food of claim 1, wherein the first film is a non-breathable film, and the second film is a breathable film.

11. The method for manufacturing an indicator for food of claim 1, further comprising attaching a release paper onto the rear surface of the second film.

12. An indicator for food formed with a first film, on which an indicator layer comprising a pH-sensitive indicator is formed, and a second film on which an adhesive layer is formed, wherein the indicator is manufactured by the method for manufacturing an indicator for food according to claim 1.

13. A packaging material for food, comprising the indicator for food according to claim 12.

14. A food packaged by the packaging material for food according to claim 13.

15. The food of claim 14, wherein the food comprises at least one food group among refrigerated meat, processed meat, and fermented food.

16. A method for checking the storage state of food using the indicator for food according to claim 12.

* * * * *